July 6, 1948. E. S. BOERNER Plant Pat. 800
ROSE PLANT
Filed Jan. 27, 1947
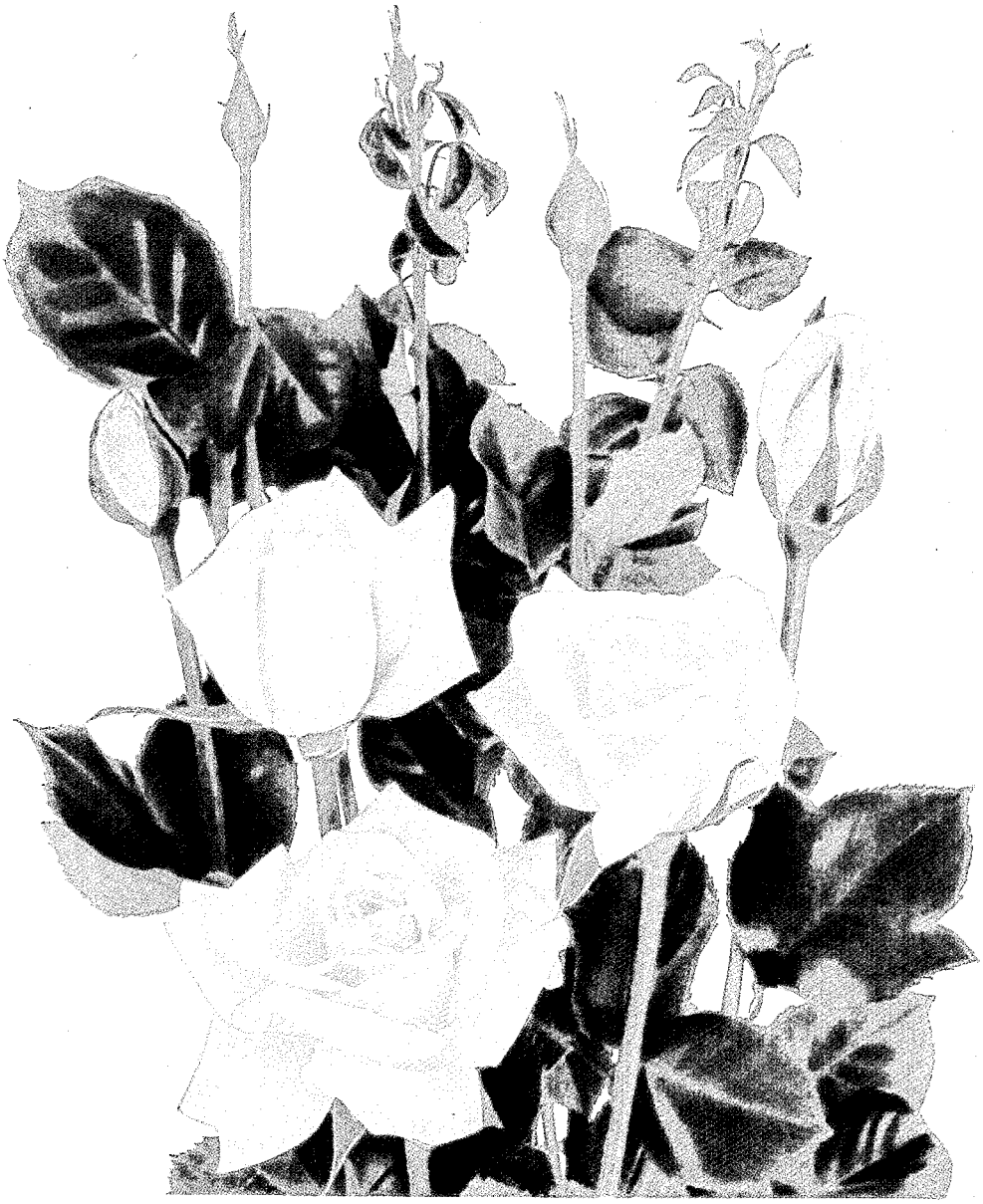
Inventor
E. S. Boerner
By Robb & Robb
Attorneys Patented July 6, 1948

Plant Pat. 800

UNITED STATES PATENT OFFICE

800

ROSE PLANT

Eugene S. Boerner, Newark, N. Y., assignor to Jackson & Perkins Company, Newark, N. Y., a corporation of New York Application January 27, 1947, Serial No. 724,623

1 Claim. (Cl. 47—61)

This invention relates to a new and distinct variety of rose plant originated by crossing an unnamed seedling with the well-known variety "Orange Nassau" (Pl. Pat. #350).

As a result of this cross, I produced a rose somewhat like "Orange Nassau" in form, but having a flower larger and unlike that of said parent, the bush itself being very vigorous and making excellent long breaks for cut flowers.

This new seedling, unlike its parent "Orange Nassau," is not prone to black spot.

Otherwise, the new variety is characterized as to novelty by the color of its blooms as hereinafter set forth; by its rich fragrance and its high-centered flower which opens gracefully and keeps for a long time as a cut flower.

Asexual reproduction of this new variety shows the foregoing characteristics come true to form and are established.

In the accompanying drawing are shown specimens of this new variety, with flowers at different stages of development from small bud to full-open bloom, and depicting the delicate shadings of their coloring as nearly as possible to reproduce.

The following is a detailed description of the new variety, color terminology being in accordance with Ridgway's Color Standard:

Parentage: Seedling.

*Seed parent.*—Seedling—unnamed (Joanna Hill × a red seedling, parentage not proved).

*Pollen parent.*—"Orange Nassau."

Classification: Botanic and commercial—hybrid tea.

*Flower*

(Observations made outdoors in fields at Newark, New York, in the morning in November 1946.)

Blooming habit: Recurrent—continuous.

Bud:

*Size.*—Large.

*Form.*—Long; pointed. Is not affected by wet or hot weather.

*Color.*—When sepals first divide—Light Salmon Orange, Plate 2. When petals begin to unfurl—Capucine Orange, Plate 3. When half blown—inside of petals—Bittersweet Pink, Plate 2; reverse of petals—Safrano Pink, Plate 2.

*Sepals.*—Serrated, branched, "hood" above bud. Curl back when petals begin to unfurl. *Color*—inside—Biscay Green, Plate 17; outside—Spinach Green, Plate 5.

*Calyx.*—Shape—pear. Size—long. Aspect—smooth. Odor when rubbed—none. Color—Scheele's Green, Plate 6.

*Peduncle.*—Length—long. Aspect—smooth. Color—Scheele's Green, Plate 6. Strength—erect; heavy.

*Opening.*—Bud opens up well. Is not affected by adverse weather conditions.

Bloom:

*Size.*—Large. Average size when fully expanded, 4".

*Borne.*—Singly.

*Stems.*—Long; strong.

*Form.*—When first open—high center. Permanence—retains its form to the end.

*Petalage.*—Double (full but open center). Number of petals under normal conditions, 30–35.

*Color.*—Center of flower—Bittersweet Pink, Plate 2. Outer petals—Orange Pink, Plate 2. Base of petals (aiglet)—Lemon Chrome, Plate 4. Inside of petals—Orient Pink, Plate 2, with Lemon Chrome, Plate 4, extending from the base. Reverse of petals—Orange Pink, Plate 2, with Lemon Chrome, Plate 4, extending from the base. General tonality from a distance—Orange Pink, Plate 2.

*Discoloration.*—General tonality at end of first day—Bittersweet Pink, Plate 2. Second day—between Bittersweet Pink, Plate 2, and Orient Pink, Plate 2. Third day—Orange Pink, Plate 2.

Petals:

*Texture.*—Thick. Is not affected by wet or hot weather.

*Appearance.* — Inside — satiny; outside — shiny.

*Form.*—Oval; pointed.

*Arrangement.*—Imbricated (regularly arranged shingle-like). Petaloids in center—few; small.

*Persistence.*—Drop off cleanly.

*Fragrance.*—Strong. Nature—tea (average hybrid tea scent).

*Lasting quality.*—On the plant and as cut flower—long.

Genital organs:

*Stamens, anthers.*—Size—large. Color—Light Cadmium, Plate 4. Arrangement—Regular around styles.

*Stamens, filaments (threads).* — Long. Color—Deep Chrome, Plate 3.

*Pollen.*—Pale Orange Yellow, Plate 3.

*Styles.*—Bunched: uneven length; short; thin.
*Stigmas.*—Martius Yellow, Plate 4.
*Ovaries.*—All enclosed in calyx.

*Plant*

Form: Bush.
Growth: Vigorous; upright.
Foliage: 5–7 leaflets.
*Size.*—Large.
*Quantity.*—Abundant.
*New foliage.*—Upper side—Oil Green, Plate 5; outer edges Victoria Lake, Plate 1. Under side—Yellowish Oil Green, Plate 5. Serrations—Victoria Lake, Plate 1.
*Old foliage.*—Upper side—Varley's Green, Plate 18. Under side—Bice Green, Plate 17.
*Shape.*—Oval pointed.
*Texture.*—Upper side — leathery. Under side—smooth. Ribs and veins—ordinary.
*Edge.*—Serrated (saw toothed).
*Serration.*—Single; small.
*Leaf stem.*—Yellowish Olive, Plate 30. Under side—prickles.

*Stipules.*—Medium length; smooth.
*Disease resistance.*—Black spot.
Wood:
*New wood.*—Biscay Green, Plate 17. Bark—smooth.
*Old wood.*—Cress Green, Plate 31. Bark—smooth.
Thorns:
*Quantity.*—On main stalks from base and on laterals from stalk—ordinary.
*Form.* — Narrow base; medium length; hooked downward.
*Color when young.*—Carmine, Plate 1.
*Position.*—Irregular.
*Prickles and hairs.*—None.

I claim:

A new and distinct variety of hybrid tea rose plant characterized as to novelty by its vigorous growing habit; resistance to black spot; delicate coloring of its flowers; rich fragrance; high-centered form of large flower and long lasting quality as a cut flower, substantially as shown and described.

EUGENE S. BOERNER.